United States Patent [19]

Sheppard et al.

[11] 4,088,642
[45] May 9, 1978

[54] COMPOUNDS HAVING BOTH PEROXY AND ALIPHATIC AZO GROUPS

[75] Inventors: Chester Stephen Sheppard, Tonawanda; Ronald Edward MacLeay, Williamsville, both of N.Y.; Richard Anthony Bafford, Aiken, S.C.

[73] Assignee: Pennwalt Corporation, Philadelphia, Pa.

[21] Appl. No.: 409,130

[22] Filed: Oct. 24, 1973

Related U.S. Application Data

[60] Division of Ser. No. 37,310, May 14, 1970, Pat. No. 3,812,095, which is a continuation-in-part of Ser. No. 703,241, Feb. 6, 1968, abandoned.

[51] Int. Cl.² ........................................... C07C 107/02
[52] U.S. Cl. ..................................... 260/174; 260/144; 260/166; 260/169; 260/239 R
[58] Field of Search ......................................... 260/174

[56] References Cited

U.S. PATENT DOCUMENTS 3,271,384   9/1966   Haas et al. ........................... 260/174
3,282,912   11/1966   Benzing ........................... 260/192 X

FOREIGN PATENT DOCUMENTS 28,459   6/1963   Japan ..................................... 260/192
988,253   4/1965   United Kingdom ................. 260/192

*Primary Examiner*—Charles F. Warren
*Attorney, Agent, or Firm*—Plumley & Tyner

[57] ABSTRACT

I. Compounds having independent peroxidic (X) and aliphatic azo groups of the formula $$[(R-N=N-R')_m-X]_n$$

Example: di-t-butylperoxy ester of cis-4,4'-azobis-(4-cyanovaleric acid).

II. A method of making a block polymer where vinyl monomer is initiated sequentially to produce in one instance: a polymer having azo-carbon linkages present, which is then reacted with vinyl monomer under conditions to rupture the azo-carbon linkages, and in another instance: a polymer having peroxy-carbon linkages present, which is then reacted with vinyl monomer under conditions to rupture the peroxy carbon linkages.

6 Claims, No Drawings

COMPOUNDS HAVING BOTH PEROXY AND ALIPHATIC AZO GROUPS

This is a division of application Ser. No. 37,310 now U.S. Pat. No. 3,812,095 filed May 14, 1970 which in turn is a continuation-in-part of copending application U.S. Ser. No. 703,241, now abandoned filed Feb. 6, 1968.

BACKGROUND OF THE INVENTION

1. Field of the Invention

This invention relates to new compounds containing independent peroxidic and aliphatic azo groups in the same molecule and to their use as sequential free radical generators in formation of polymers.

2. Description of the Prior Art

The combination of an azo group and a peroxide group in the same molecule, however, is not new. The following such compounds have been reported:

$$(CH_3)_3COO\overset{O}{\overset{\|}{C}}-N=N-\overset{O}{\overset{\|}{C}}OC_2H_5 \quad (1)$$

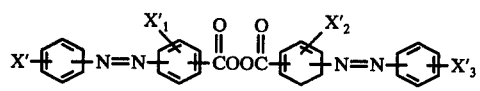
(2)

where $X', X'_1, X'_2, X'_3$ can be $H-, NO_2, NH_2, I, C_2H_5O-$,

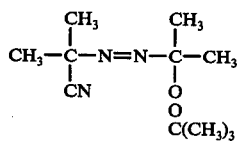
(3,4)

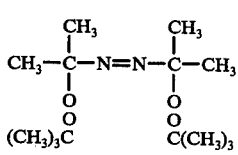
(4)

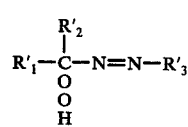
(5)

where $R'_1, R'_2,$ and $R'_3$ are organic radicals which are inert to azo and hydroperoxide radicals.

None of these known azo-peroxides are useful as sequential free radical generators and such a use for these compounds has not been suggested. Compound (2) has been reported to be a low temperature polymerization initiator. Compounds (3) and (4) have also been reported to be initiators of vinyl polymerization. Compounds of structure (5) are reported to be photo- and thermalpolymerization initiators i.e. they will generate free radicals either by irradiation or by heating, which is typical for conventional azo and peroxide initiators. In each of these compounds (1), (3), (4) and (5), the peroxy and azo groups are attached to the same carbon atom. Thus, these compounds undergo simultaneous azo and peroxide decomposition and consequently cannot be used as sequential free radical generators in the manner that the novel compounds of the present invention can be used. The compounds of this invention contain azo and peroxide groups which are not linked to the same carbon atom and therefore sequential decomposition can and does occur, as illustrated in the Examples.

In compound (2), the azo portion of the molecule is not a free radical generator, at least in the broad temperature range where vinyl polymerizations are conventionally carried out. The peroxide portion is a free radical generator useful for vinyl polymerizations. The azo portion in this structure is attached to two phenyl or substituted phenyl radicals and structures of this type are typical azo dyes. These structures are known to be stable and absorb certain wavelengths of visible light. Thus, the azo portion of compound (2) can be used to activate the peroxide portion by visible light and it can also be used as a dye to impart color, but it does not decompose to give free radicals under conventional vinyl polymerization conditions. Compounds of structure (2) cannot be used as sequential free radical generators in the manner that the novel compounds of the invention can be used.

(1) Japanese Pat. No. 28,459 issued 12/16/65 by H. Minato (to Teijin Ltd.); C.A. 64, 11090h (1966).
(2) U.S. Pat. No. 3,271,384 issued 9/6/66 to Polaroid Corporation.
(3) British Pat. No. 988,253 issued 4/7/65 to Monsanto Company.
(4) Canadian Pat. No. 750,380 issued 1/10/67 to Monsanto Company.
(5) (a) U.S. Pat. No. 3,278,304 issued 10/11/66 to Gevaert Photo-Production N.V. (b) British Pat. No. 1,054,125 issued 1/4/67 to same assignee.

SUMMARY OF THE INVENTION

I. Compounds

The compounds of the invention include independent peroxidic and aliphatic azo groups and have the formula:

$$[(R-N=N-R')_m-X]_n$$

where
(1) $m$ is an integer equal to 1-2;
(2) $n$ is a number equal to 1-10;
(3) R' is

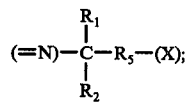

(4) X is a peroxy containing radical selected from

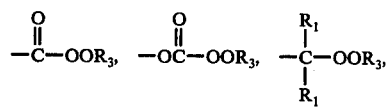

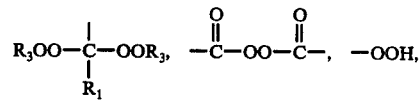

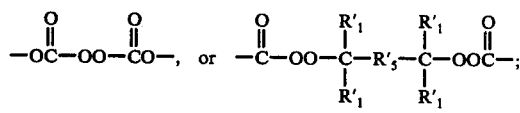

(5) $R_1$ and $R'_1$ may be the same or different and are alkyl or cycloalkyl radicals having 1-10 carbon atoms;

$R_2$ is selected from (6)

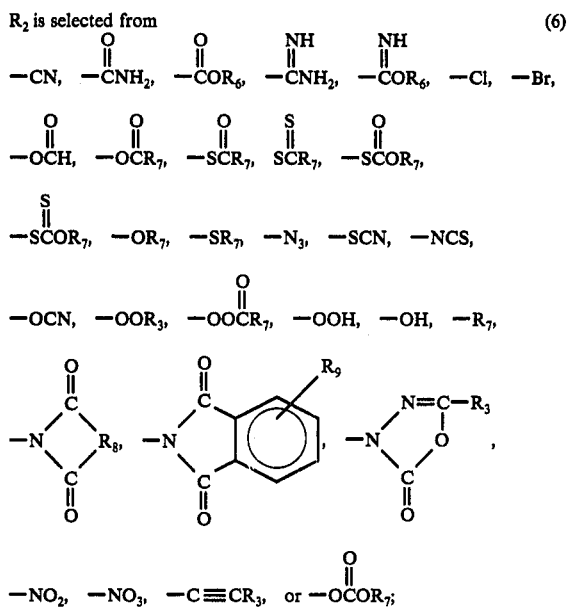

(7) $R_3$ is a tertiary aliphatic radical having 4–10 carbon atoms;
(8) $R_5$ and $R'_5$ may be the same or different and are aliphatic diradicals having 1–20 carbons which diradicals optionally contain in the backbone structure one or more non-adjacent oxygen, sulfur or nitrogen atoms; aromatic diradicals having 6–12 carbons; or aromatic-aliphatic diradicals having 7–20 carbons optionally containing in the backbone structure one or more non-adjacent oxygen, sulfur or nitrogen atoms;
(9) $R_6$ is a lower alkyl radical (normally containing 1–6 carbon atoms);
(10) $R_7$ is an alkyl or cycloalkyl radical of 1–10 carbons or an aromatic radical of 6–12 carbons;
(11) $R_8$ is a lower alkylene diradical (usually having 1–8 carbons);
(12) $R_9$ is hydrogen, an alkyl or cycloalkyl radical of 1–10 carbons, or an aromatic radical of 6–12 carbons;
(13) $R_1$ and $R_5$ together with the tertiary carbon atom in $R'$ can form a cycloalkyl triradical of 3–10 carbons; and
(14) R is (a) a tertiary aliphatic radical of 4–10 carbons, (b) $R'$-X or (c) $R'$ when $m$ is 1 and X is a diradical.

SUMMARY OF THE INVENTION

II. Methods of Polymerization

A. One method of the invention prepares a block polymer by:
(1) forming a polymer having azo groups present by reacting vinyl-type monomer and an azo-peroxy compound as above under vinyl polymerization conditions, controlling conditions in order to cause the peroxy-oxygen linkages to rupture prior to rupture of the azo-carbon linkages, said rupture of the peroxy-oxygen linkages having the effect of initiating said polymerization; and
(2) reacting vinyl-type monomer with the polymer of step (1) under conditions to rupture the azo-carbon linkages of said step (1) polymer to produce a block polymer product.

B. Another method of the invention prepares a block polymer by:
(1) forming a polymer having peroxy groups present by reacting vinyl-type monomer and an azo-peroxy compound as above under vinyl polymerization conditions, controlling the conditions in order to cause the azo-carbon linkages to rupture prior to rupture of the peroxy-oxygen linkages, said rupture of the azo-carbon linkages having the effect of initiating said polymerization; and
(2) reacting vinyl-type monomer with the polymer of step (1) under conditions to rupture the peroxy-oxygen linkages of said step (1) polymer to produce a block polymer product.

DETAILED DESCRIPTION OF THE INVENTION

I. Compounds

The compounds of the invention have the general formula $$[(R\text{-}N=N\text{-}R')_m\text{-}X]_n$$

and may be "simple" compounds, when $n$ is 1 and $m$ is 1 or 2, or "polymeric" compounds when $n$ is 2–10.

In the definition of $R'$ as the diradical

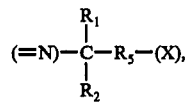

the azo nitrogen (=N) and peroxy radical (X) are shown in order to set out the relation of the groups to the $R'$ group.

$R_1$ and $R'_1$ can be any aliphatic or cycloaliphatic radical having up to 10 carbon atoms or more. Commonly they are alkyl radicals.

X and $R_3$ are as defined in the aforesaid Summary of the Invention (I. Compounds).

$R_2$ can be any aliphatic, cycloaliphatic, or aromatic radical, particularly an alkyl, phenyl, or cyano radical, and also an alkoxy, aryloxy, acyloxy, alkoxycarbonyl, alkoxycarbonyloxy, aroyloxy, carbamoyl, azido, chloro, bromo, thiocyanato, isothiocyanato, thioacyloxy, dithioacyloxy, alkoxyimidoyl, amidoyl, alkoxythiocarbonyloxy, alkoxydithiocarbonyloxy, alkylthiol, arylthiol, cyanato, tertiary alkylperoxy, acylperoxy, hydroperoxy, hydroxyl, nitro, nitrato, diacylimido, 2-substituted-1,3-4-oxadiazol-4-yl, and alkyl or arylacetylino radical.

$R_5$ and $R'_5$ can be any aliphatic or aromatic-aliphatic diradical having up to 20 carbons and optionally containing one or more non-adjacent oxygen, sulfur, or nitrogen atoms in the backbone structure, or an aromatic diradical having 6 to 12 carbons.

$R_6$ is an alkyl radical normally containing 1 to 6 carbons.

$R_7$ can be any aliphatic, cycloaliphatic, or aromatic radical, particularly a lower alkyl of 1 to 6 carbons and a phenyl or a lower alkyl and a chlorine substituted phenyl radical.

$R_8$ can be any aliphatic diradical, particularly a lower alkylene diradical containing up to 8 carbons.

$R_9$ can be hydrogen or any aliphatic, cycloaliphatic or aromatic radical, particularly a lower radical of 1 to 6 carbons and a phenyl or substituted phenyl radical.

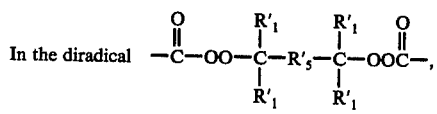

$R_5$, one tertiary carbon and one $R_1$ together can form a 5 cycloaliphatic diradical.

R can be (a) a tertiary aliphatic/radical having 4–10 carbon atoms, particularly a t-alkyl radical, or (b) the combination radical R'-X or (c) when $m$ is 1 and X is a diradical included in the above definition, R can be R'.

The compound may be open-ended or may be closed, i.e., cyclic. Example 1 shows a cyclic compound where R=R'——(CN)C(CH$_3$)CH$_2$CH$_2$-; $m=n=1$; and X is —(O)-COO-C(O)—.

Several illustrative compounds of the invention are prepared in the working examples set forth herein.

Utility

The compounds of the invention may be used in any operation or reaction where a corresponding azo compound, in the absence of the peroxy group, or a corresponding peroxy compound, in the absence of the azo group, could be used — taking into account the effect of the azo group which is present. Thus these compounds can be used as cure initiators for mixtures of vinyl monomers and unsaturated polyester resins. Importantly, they are initiators for polymerization reactions, especially polymerization of vinyl-type monomers. The initiator may be selected to give simultaneous, or essentially so, rupture of both the azo and peroxy groups or give sequential rupture. The use of compounds having different rates of rupture at a given condition permits the formation of polymers having either azo groups or peroxy groups as a part of the polymer. These polymers are ideal for the preparation of block or graft polymers and this is a preferred use of the compounds of the invention. Examples 6, 7 and 20 illustrate this preferred aspect of the invention.

Methods of Preparation

The compounds of this invention can be prepared by one or more of the following general techniques:

(A) The peroxidation of suitably substituted aliphatic azo compounds (an especially suitable class of such azo compounds are those that contain acylating functionalities e.g. acid chloride, choroformate, and anhydride groups); of acid chlorides or anhydrides to diacyl peroxides or to peroxyesters; of chloroformates to peroxydicarbonates or to monoperoxycarbonates; of ketones to diperoxyketals; and of tertiary alcohols to dialkyl peroxides or hydroperoxides (Examples 1–5, 9, 11, 13–16, 28 and 36–45).

(B) The coupling of a peroxide and an aliphatic azo compound each containing a functional group that will interact to link the azo to the peroxide. Coupling reactions are well known to the art and involve well known organic reactions such as esterification, amidation, etherification, carbonate formation and many others. Especially suitable compounds for these coupling reactions are azo compounds containing acylating functions; peroxides containing acylating functions; hydroxy containing diperoxyketals; and other various known peroxides and azo compounds containing functionalities such as carboxy and hydroxy groups (Examples 10, 12, and 18–20).

(C) The conversion of the ketone group in peroxides containing a ketone functional group to an aliphatic azo compound. (Examples 21–27 and 29–35).

Description

II. Methods of Polymerization

The method inventions are directed to the use of compounds of the invention to prepare block polymers by a sequential procedure wherein a compound I is used to initiate vinyl polymerization to prepare a polymer including either azo or peroxy groups as a part of the polymer — as determined by the condition under which the polymerization is carried out. The azo or peroxy group containing polymer is then further polymerized with vinyl monomer under conditions to rupture the azo or peroxy group whereby the block polymer is formed.

These sequential and/or preferential decompositions of the azo and peroxide portions of the molecule can be accomplished by a variety of techniques. One method is to use two different temperatures, taking advantage of the difference in the thermal rates of decomposition of the azo and peroxide portions of the molecule. Another method, also based on the different thermal rates of decomposition, is to use the same temperature but different reaction times. For example, the peroxide portion of the azo-peroxide of Example 3 would be 50% decomposed after 13 minutes at 70° C while the azo portion would be less than 4% decomposed in this time, but the latter would be 50% decomposed after 179 minutes at this same temperature.

Still another method is to use an activator for the peroxide portion, e.g. amines, transition metal salts, etc., which will keep the azo portion intact since the azo structures in Compound I are insensitive to such activators. The azo portion can then be subsequently decomposed either thermally or by irradiation (e.g. ultraviolet). Still another technique is to decompose one portion (either azo or peroxide) thermally and subsequently decompose the other portion by irradiation or vice-versa. Another method is to use two different irradiation sources in sequence where one source preferentially attacks one portion and the second radiation source preferentially attacks the other portion of the azo-peroxide molecule.

Thus, by taking advantage of the difference in the physical and chemical properties of the novel azo-peroxides of Compound I, a variety of techniques can be used for sequential free radical generation. Sequential free radical generation is very useful in the vinyl polymerization field. Block copolymers can be made from any combination of polymerizable vinyl monomers.

Sequential free radical generation is also employed in the conventional polymerization of ethylene and styrene. The present art accomplishes this by using two or more polymerization initiators of different thermal stability.

Any vinyl-type monomer that can be polymerized by free-radicals can be used to prepare the azo- or peroxide-containing polymers and any combination of different vinyl monomers can be used to make the block polymers. Typical vinyl monomers include: styrene, vinyl chloride, vinyl acetate, ethyl acrylate, methyl methacrylate, butadiene acrylonitrile, acrylamide, acrylic acid, methacrylic acid, vinyl carbazole, vinyltoluene, vinylpyridine, vinylidene chloride and the like.

Conventional polymerization techniques, i.e. bulk, solution, suspension or emulsion polymerizations, can be used. The choice will depend upon the normal reasons for choosing one technique over another e.g. water and oil solubility of the monomer and/or initiator; desired molecular weight range of the polymer; temperature (or exotherm) control; etc.

The temperatures at which the polymerizations are carried out will depend upon the polymerization technique; the monomer, solvent or suspending medium; and the physical properties desired in the polymer; but most of all upon the azo-peroxide initiator and the method chosen to decompose the azo or peroxide portion of the initiator. Activation of the peroxide portion by amines, reducing agents, transition metal carboxylates, etc., can be carried out from below $-20°$ C up to its normal decomposition temperature. The same is true for activation of the peroxide or azo portions by irradiation. Irradiation sources can be ultra-violet radiation, and in the presence of photosensitizers (e.g. certain azo dyes) visible light can also be used. The temperatures used for the thermal decompositions of the azo or peroxide portions will depend upon the thermal stability (half-life) of the azo or peroxide grouping in the molecule. These half-lives can be determined quantitatively for each azo-peroxide compound by conventional methods i.e. gas evolution, and iodometric, ultra-violet, or gas chromatographic analytical techniques to determine the rate of disappearance of each portion (azo or peroxide) at any given temperature. (Such half-life data were determined for the compounds made in Examples 1 to 5.)

However, it is not necessary to accurately determine the half-life of each portion since most half-lives can be predicted, within a few degrees, from the closest analogous monomeric azo or peroxide structure, many of which are well known. Such ten-hour half-life temperature ranges of some typical peroxide and azo structures are given in Tables I and II. (More accurate data is available on the individual compounds where R, R', R" and R''' are known and such data was used to estimate the half-life ranges on the compounds prepared in Examples 8 to 19.)

There are many literature references to fill in the conditions for carrying out the methods as a matter of ordinary skill i.e. all the vinyl monomers can be polymerized by a peroxide or azo initiator; azo and peroxide initiators are commonly used in all four free-radical polymerization techniques; and it is old in the art to activate peroxides with amines, transition metal salts, reducing agents and to activate both azo and peroxide initiators with ultra-violet radiation or visible light in the presence of photosensitizers.

TABLE I
Ten-Hour Half-Life Temperature Ranges of Various Peroxides

| Peroxide Class | General Structures | 10 Hour Half-Life Range °C |
|---|---|---|
| t-Alkyl Peroxyesters | $R'CH_2COOR$ (O) | 102 |
| | $R''CHCOOR$ with $R'$ (O) | 66–79 |
| | $R''-C(R''')(R')-COOR$ (O) | 54–55 |
| | $>C=C-COOR$ (O) | 98–105 |
| Diacyl Peroxides | $(R'CH_2CO-)_2$ (O) | 61–69 |
| | $(R''-CH(R')-CO-)_2$ (O) | 27–34 |
| | Aryl-C(O)-O- with $X_n$ | 54–75 |
| Dialkyl Peroxides | $R''-C(R''')(R')-O-O-C(R''')(R')-R''$ | 117–128 |
| Diperoxyketals | $R''(OOR)/R'(OOR)$ C | 101–110 |
| O-Alkyl O,O-t-Alkyl Monoperoxycarbonates | $R'OCOOR$ (O) | 99 |
| Peroxydicarbonates | $R'OCOOCOR'$ (O)(O) | 45 |
| Hydroperoxides | ROOH | 155–172° C* | where: R = t-alkyl radical
R', R", R''' = aliphatic or aromatic radicals.
* Alkyl- and aralkyl hydroperoxides are more generally used at low temperatures in combination with redox catalysts in emulsion vinyl monomer polymerizations.

TABLE II
Ten-Hour Half-Life Temperatures of Various Azo Compounds

| General Structures | 10 Hour $t_{\frac{1}{2}}$ range, °C |
|---|---|
| $CH_3-C(CH_3)(CN)-N=N-C(CH_3)(CN)-CH_3$ | 65 |
| $t-C_4H_9-N=N-C(R)(CN)-R'$ | | when:
| | |
|---|---|
| $R=R'=CH_3$ | 79 |
| $R=CH_3$; $R'=(CH_3)_2CHCH_2$ | 72.8 |
| $R=R'=(CH_3)_2CHCH_2$ | 56 |
| $R=CH_3$; $R'=ROCCH_2CH_2$ (O) | 76–79 |
| $R=CH_3$; $R'=RCOCH_2$ (O) | 77–80 |
| $R + R' = -(CH_2)_5-$ | 96.3 |
| $R + R' = -(CH_2)_7-$ | 55 |

TABLE II-continued

Ten-Hour Half-Life Temperatures of Various Azo Compounds

| General Structures | 10 Hour $t_{\frac{1}{2}}$ range, ° C |
|---|---|
| 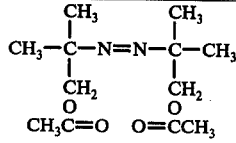 | 162 |

EXAMPLES

Illustrative embodiments of compounds of the invention and uses of some of these in methods of the invention are set forth in the following examples, which are not to be considered as limiting the scope of the invention.

EXAMPLE 1

Preparation of 6,9-Dimethyl-6,9-dicyano-Δ$^7$,1,2-dioxa-7,8-diazacyclododecan-3,12-dione.

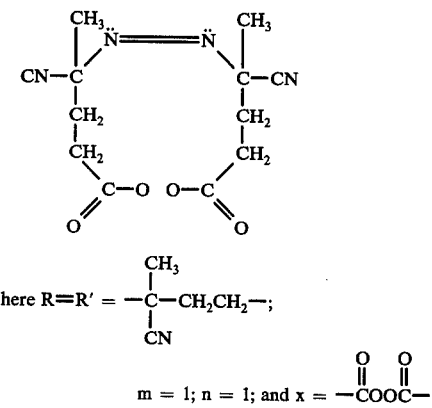

Compound I where R=R' = —C(CH$_3$)(CN)—CH$_2$CH$_2$—;

m = 1; n = 1; and x = —COOC—.

To a solution containing 2.0 g. (0.028 mole) of 50% hydrogen peroxide and 4.8 g. (0.0616 mole) of 50% sodium hydroxide in 100 ml. of water was added 30 ml. of methylene chloride. The resulting mixture was cooled to 10° C and stirred while a solution containing 8.4 g. (0.0264 mole) of the diacid chloride of cis-4,4'-azobis-(4-cyanovaleric acid) in 50 ml. of methylene chloride was added during a 40 minute period, keeping the reaction temperature at 8° to 10° C throughout the addition. The reaction mixture was stirred for an additional 3 hours at 0° C to 10° C. Then, 30 ml. of a saturated solution of sodium bicarbonate was added, and the reaction mixture stirred for 15 minutes at 10° C. The methylene chloride layer was separated, cooled to 0° to 3° C, and washed twice with 40 ml. solutions of 5% sodium bicarbonate, then three times with 20 ml. solutions of 3% potassium hydroxide, then twice with water, dried over anhydrous sodium sulfate and filtered. The resulting methylene chloride solution was concentrated to about 40 ml. and allowed to stand at −20° C to crystallize for several days. The methylene chloride solution was decanted and the white solid remaining was dried under vacuum at 0° C. The methylene chloride solution was concentrated further and again stored at −20° C to obtain a second crop of crystallized product. The combined products weighed 2.6 grams (35.4% yield) and additional product was still present in the methylene chloride mother liquors.

The product did not melt upon heating to 103° C at which point it exploded with a loud pop. Its infrared spectrum was in agreement with the structure of 6,9-dimethyl-6,9-dicyano-Δ$^7$,1,2-dioxa-7,8-diazacyclododecan-3,12-dione, showing absorption bands for the cyano and diacyl peroxide groups. The product is sensitive to shock and decomposition rate studies indicated that the diacyl peroxide portion decomposed at a significantly faster rate ($t_{1/2} \approx 99$ minutes at 70° C) than the azo portion of the molecule ($t_{1/2} \approx 236$ minutes at 70° C) in o-dichlorobenzene. The product can be stored at −20° C for more than one month.

EXAMPLE 2

Preparation of the Polymeric Peroxide of trans-4,4'-Azobis(4-cyanovaleric acid) Terminated with Carboxylic Acid Groups.

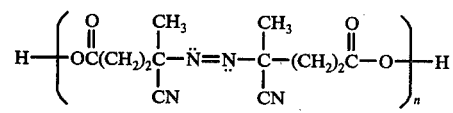

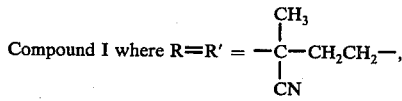

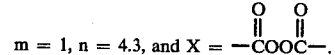

To a stirred solution containing 2.29 g. (0.057 mole) of sodium hydroxide and 0.965 g. (0.028 mole) of hydrogen peroxide in 30 ml. of water was added a mixture containing 3.0 g. of sodium dihydrogen phosphate, 3.0 g. of disodium hydrogen phosphate and 60 ml of water at 0° to 5° C. To this stirred solution was added, dropwise, over 25 minutes, a solution of 8.5 g. (0.027 mole) of the diacid chloride of trans-4,4'-azobis(4-cyanovaleric acid) in 60 ml. of methylene chloride keeping the temperature below 3° C throughout the addition. The reaction was stirred cold for an additional 1½ hours and then filtered. The solid product was washed with methylene chloride and water and then dried. It weighed 4.9 g. (66.2% yield) and had an active oxygen content (determined by iodometric titration) of 4.4% which corresponds to an average n value in the above structure of 4.3. The product was sensitive to shock and decomposed at 106° C with a loud pop.

An additional 1.8 g. (24.3% yield) of lower molecular weight product (average n = 1.585) with an active oxygen content of 1.68% was obtained from the aqueous-methylene chloride filtrate by evaporating off the methylene chloride with a stream of nitrogen gas. This product was less shock sensitive than the first isolated product above.

The infrared spectra of both products were in accord with the above structure. Decomposition rate studies on the first product indicated that the peroxide linkages decomposed significantly faster ($t_{1/2} \approx 369$ minutes at 60° C and 102 minutes at 70° C) in water than the azo linkages ($t_{1/2} \approx 860$ minutes at 60° C and 231 minutes at 70° C).

This product cured an unsaturated polyester resin-styrene material at 100° C to a hard thermoset.

EXAMPLE 3

Preparation of the Polymeric Peroxide of trans-4,4'-Azobis(4-cyanovaleric acid) Terminated with Sodium Carboxylate Groups.

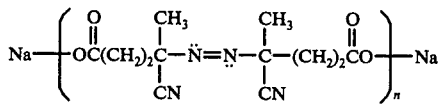

Compound I where R=R' = $-\underset{\underset{CN}{|}}{\overset{\overset{CH_3}{|}}{C}}-CH_2CH_2-$;

m = 1, n = 2.62, and X = $-\overset{\overset{O}{\|}}{C}O\overset{\overset{O}{\|}}{C}-$.

To a stirred solution containing 0.72 g. (0.018 mole) of sodium hydroxide and 0.225 g. (0.0066 mole) of hydrogen peroxide in 13 ml. of water was added, dropwise, a solution containing 1.9 g. (0.006 mole) of the diacid chloride of trans-4,4'-azobis(4-cyanovaleric acid) in 12 ml. of methylene chloride at 0° to 5° C. A white precipitate formed. The reaction mixture was stirred for two hours and then filtered. The solid product was washed with water and methylene chloride and then dried under vacuum. It weighed 0.8 g. (41.2% yield) and decomposed at 97° C with a loud pop.

The product was sensitive to shock and its infrared spectrum was in agreement with the above structure. The active oxygen content, determined by iodometric titration, was found to be 3.27%, which corresponds to an average n value in the above structure of 2.62.

The product is partially soluble in water and decomposition rate studies in water indicated that the peroxide linkages decomposed significantly faster ($t_{1/2} \approx 13$ minutes at 70° C) than the azo linkages ($t_{1/2} \approx 179$ minutes at 70° C).

EXAMPLE 4

Preparation of the Di-t-butylperoxy Ester of cis-4,4'-Azobis(4-cyanovaleric acid).

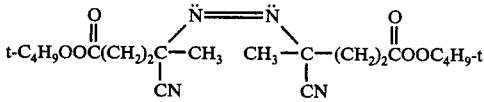

Compound I where R=R'X and R' =
$-\underset{\underset{CN}{|}}{\overset{\overset{CH_3}{|}}{C}}-(CH_2)_2-$, X = $\overset{\overset{O}{\|}}{C}OOC_4H_9\text{-}t$, m = 1, and n = 1.

To a solution containing 3.8 g. (0.012 mole) of the diacid chloride of cis-4,4'-azobis(4-cyanovaleric acid) in 40 ml. of methylene chloride was added 2.18 g. (0.024 mole) of 99.3% pure t-butyl hydroperoxide at 0°–5° C. The resultant solution was stirred at 0°–5° C while 1.9 g. (0.024 mole) of pyridine in an equal volume of methylene chloride was added. The reaction mixture was stirred at 0°–3° C for 4¾ hours and then allowed to warm to 21° C at which point it was cooled to below 10° C and washed with 20 ml. water. The cold methylene chloride reaction solution was then given the following washings: 1) once with 20 ml. of dilute hydrochloric acid; 2) once again with 20 ml. of water; 3) once with 20 ml. of a 5% sodium sulfite and 5% sodium acetate solution; 4) twice with 20 ml. of a 5% sodium bicarbonate solution; and 5) twice with 20 ml. of water. The resultant methylene chloride solution was dried over magnesium sulfate, filtered, and the methylene chloride evaporated to obtain 4.0 g. (78.6% yield) of the di-t-butylperoxy ester of cis-4,4'-azobis(4-cyanovaleric acid) m.p. 104°–106° C with decomposition.

The product had an active oxygen content (found by iodometric titration) of 7.37% indicating a purity of 97.7%. The infrared spectrum of the product was in agreement with the above structure showing perester carbonyl and t-butylperoxy absorption bands and no carboxylic acid, acid chloride or hydroxyl absorption bands.

The product's infrared spectrum was not changed after standing for two days at 21° C indicating room temperature stability. It was only moderately sensitive to shock. Decomposition rate studies in trichlorobenzene indicated that the azo portion decomposed at a significantly faster rate ($t_{1/2} \approx 92$ minutes at 80° C) than the perester portion of the molecule ($t_{1/2} \approx 319$ minutes at 80° C).

EXAMPLE 5

Preparation of the mono-t-Butylperoxy Ester of the Diacid Chloride of trans-4,4'-Azobis(4-cyanovaleric acid).

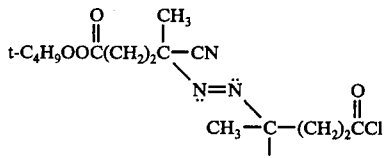

Compound I where m = 1, n = 1, and R = $Cl\overset{\overset{O}{\|}}{C}-(CH_2)_2\underset{\underset{CN}{|}}{\overset{\overset{CH_3}{|}}{C}}-$, R' = $-\underset{\underset{CN}{|}}{\overset{\overset{CH_3}{|}}{C}}-(CH_2)_2-$, and X = $-\overset{\overset{O}{\|}}{C}OOC_4H_9\text{-}t$.

To a stirred cold (0°–2° C) solution containing 2.18 g. (0.024 mole) of 99.3% pure t-butyl hydroperoxide and 1.35 g. (0.024 mole) of potassium hydroxide in 41.5 ml. of water was added, over a ten minute period, a solution containing 3.8 g. (0.012 mole) of the diacid chloride of trans-4,4'-azobis(4-cyanovaleric acid) in 30 ml. of methylene chloride, keeping the reaction temperature at 0°–2° C throughout the addition. The reaction mixture was stirred cold for an additional 18 minutes and the layers were then separated. The methylene chloride layer was washed twice with 10 ml. portions of a 5% sodium bicarbonate solution, once with water, dried over magnesium sulfate, and filtered. The methylene chloride solvent was evaporated to obtain 4.6 g. (theory = 4.5 g.) of a low melting product.

Recrystallization from benzene-pentane at −7° C gave 2.55 g. of product that had an active oxygen content of 4.30% (theory = 4.32%). Its infrared spectrum was in agreement with the above structure showing both peresters and acid chloride carbonyl absorption bands. Decomposition studies in dioctyl phthalate at 90° C indicate that both the azo and perester linkages decompose simultaneously at this temperature, the product having a half-life of about 28 to 32 minutes. Apparently, the perester undergoes induced decomposition at this relatively high temperature.

EXAMPLE 6

A. Preparation of an Azo Containing Polystyrene Using the Azo-Peroxide Initiator of Example 1.

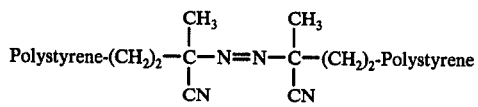

To 20 g. of styrene was added 0.7285 g. of 6,9-dimethyl-6,9-dicyano-$\Delta^7$, 1,2-dioxa-7,8-diazacyclododecan-3,12-dione (from Example 1) dissolved in 3 g. of methylene chloride. The reaction mixture was kept under nitrogen in a sealed tube at 50° C for 24 hours and then dissolved in benzene. The polystyrene was obtained by precipitation from the benzene solution by adding methanol. It was again taken up in benzene and reprecipitated with methanol. After still another reprecipitation, 5.245 g. of azo containing polystyrene was obtained.

A blank, run under the same conditions but without an initiator, gave only a 0.5% conversion of styrene to polystyrene by thermal polymerization.

B. Preparation of a Polystyrene-Poly(methyl methacrylate) Block Copolymer from the Azo-Containing Polystyrene of A.

A mixture of 9 g. of methyl methacrylate and 1 g. of the azo-containing polystyrene from A above was heated at 75° C under nitrogen in a sealed tube for 7 hours. The resultant reaction mixture was taken up in benzene and the block copolymer precipitated with petroleum ether. After drying, it weighed 4.5 grams. Its infrared spectrum showed the characteristic absorption bands of polystyrene and poly(methyl methacrylate).

In a blank run, methyl methacrylate gave no polymer after 7 hours at 75° C.

Further evidence for the formation of a polystyrene-poly (methyl methacrylate) block copolymer was obtained from demixing tests as shown below:

|  | Control 14% Solids | Test #1 21% Solids | Test #2 14% Solids |
|---|---|---|---|
| Polystyrene Homopolymer | 0.614g. | 0.614g. | 0.614g. |
| Poly(methyl methacrylate) Homopolymer | 0.614g. | 0.614g. | 0.614g. |
| Polystyrene-Poly(methyl methacrylate) Block Copolymer | — | 0.614g. | 0.614g. |
| Chloroform | 8.772g. | 8.772g. | 13.158g. |
| Demixing Time | 0.5 Hour | >145 Hrs. | 41 Hours |

The ability to stabilize is tested in the laboratory by empirical tests where the "stabilized" solution is compared to a control solution. The time for the appearance of two distinct layers is measured. It is to be emphasized that the results cannot be used to compare effectiveness in different polymeric systems, since even polymer molecular weight can cause substantial changes in separation time between two systems made from the same monomers. However the laboratory tests are meaningful in terms of screening potential stabilizers.

It is known that when two different polymers are brought in solution — really a dispersion — in a common solvent, over a period of time the solution (dispersion) segregates into two layers (demixes), having different polymeric compositions. Apparently homogeneous melts of two different polymers frequently on solidifying show undesired segregation or heterogeneous dispersion of one polymer throughout the continuous phase of the other polymer. Since physical mixtures (dispersion) of two different polymers afford very desirable physical properties, if a homogeneous mass is maintained, stability of the dispersion is of importance. A "third" component of the mix which improves the dispersion stability of the mix is known as a stabilizer — in certain special areas, the stabilizer is referred as a compatibilizing agent.

EXAMPLE 7

A. Preparation of a Peroxide-Containing Polystyrene Using the Azo-Peroxide Initiator of Example 4.

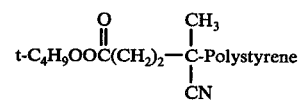

A solution of 5 g of styrene and 1 g of the di-t-butylperoxy ester of cis-4,4'-azobis(4-cyanovaleric acid) (from Example 4) was heated at 70° C under nitrogen in a sealed tube for 110 minutes. The cooled reaction mixture was dissolved in benzene and poured into methanol to precipitate the peroxide-containing polystyrene, which after drying, weighed 3.2 g.

Its infrared spectrum showed the characteristic absorption bands for polystyrene and the t-butylperoxy ester groups.

B. Preparation of a Polystyrene-Poly(methyl methacrylate) Block Copolymer from the Peroxide-Containing Polystyrene of A.

A mixture of 2g. of methyl methacrylate and 1 g. of the peroxide-containing polystyrene from A above was heated at 85° C under nitrogen in a sealed tube for 3 hours. After cooling, the resultant reaction mixture was dissolved in a benzene-acetone solvent mixture and the poly(methyl methacrylate) homopolymer precipitated out by adding hexane, and filtered off. Removal of the solvents from the filtrate under vacuum left 0.8 g. of the block copolymer.

Its infrared spectrum showed the characteristic absorption bands of polystyrene and poly(methyl methacrylate).

Further evidence for the formation of a polystyrenepoly(methyl methacrylate) block copolymer was obtained from the demixing tests shown below:

|  | Control 5.3% Solids | Test 5.3% Solids |
|---|---|---|
| Polystyrene Homopolymer | 1g. | 1g. |
| Poly(methyl methacrylate) Homopolymer | 1g. | 1g. |
| Polystyrene-Poly(methyl methacrylate) Block Copolymer | — | 0.7g. |
| Chloroform | 37.5g. | 51g. |
| Demixing Time | 30 mn. | 150 min. |

EXAMPLE 8

Preparation of Di[4-t-Butylazo-4-cyanovaleryl] peroxide.

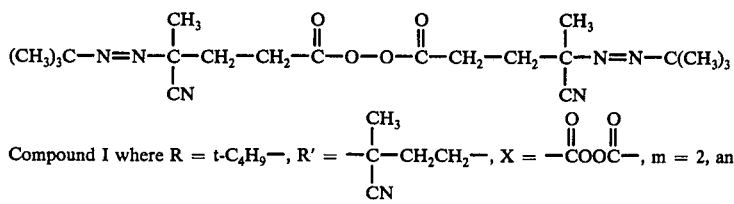

Compound I where R = t-C₄H₉—, R' = —C(CH₃)(CN)—CH₂CH₂—, X = —COOC—, m = 2, and n = 1.

To a solution of 0.48 g. (.012 m) of sodium hydroxide and 0.40 g. (.006 m) of 50% hydrogen peroxide in 10 ml. water at 10° C was added a solution of 2.7 g. (.0118 m) of 4-t-butylazo-4-cyanovaleryl chloride in 10 ml. benzene over 5 minutes. After the addition was complete, the reaction was stirred an additional ½ hour at 10° C and 15 minutes more allowing the temperature to rise to 23° C. Another 10 ml. benzene was added, the benzene layer separated, washed with 30 ml. 10% NaHCO₃ solution, 15 ml. water, dried over anhydrous sodium sulfate, filtered and the benzene stripped off. A white crystalline solid weighing 2.3 g. (93% yield) resulted.

The product had a melting point of 87°–88° C with decomposition, 91°–92° C after recrystallization from benzenepentane. The material assayed 100% by HI analysis. The product was not shock sensitive and its infrared spectrum was in agreement with that of the desired product.

The azo portions of the molecule have a 10 hour half-life at approximately 76° C while the peroxide portion has a 10 hour half life at approximately 63° C.

EXAMPLE 9

Preparation of t-Butyl 4-t-butylazo-4-cyanoperoxyvalerate

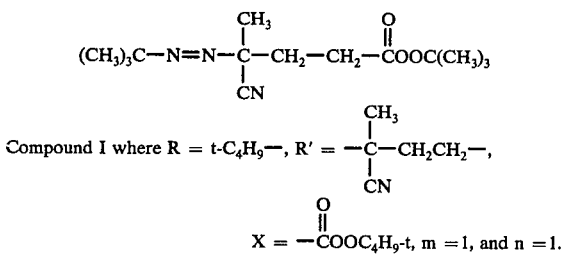

Compound I where R = t-C₄H₉—, R' = —C(CH₃)(CN)—CH₂CH₂—,

X = —COOC₄H₉-t, m =1, and n =1.

To a solution of 2.7 g. (.03 m) of 99% t-butylhydroperoxide in 15 ml. water at 5° C was added 3.74 g. (.03 m) 1 of 45% KOH. The solution was cooled to 3° C and a solution of 6.3g. (.0275 m) of 4-t-butylazo-4-cyanovaleryl chloride in 10 ml. benzene was added over ½ hour holding the temperature between 3° and 5° C. After the addition was over, the reaction was stirred an additional hour at room temperature. The benzene layer was separated, washed twice with 10% NaHCO₃ solution, once with water, dried over anhydrous sodium sulfate, filtered and the benzene stripped off. A liquid weighing 6.8g. (88% yield) was obtained.

The product assayed 88½% by an iodometric analysis. The infrared spectrum was in agreement with that of the desired product and there was no indication of any residual t-butyl hydroperoxide present. The product was not shock sensitive. It slowly evolved nitrogen at 90° C.

The azo portion of the molecule has a 10 hour half-life at approximately 76° C, while the peroxide portion has a 10 hour half-life above 102° C.

EXAMPLE 10

Preparation of 1,3-Dimethyl-3-(t-butylperoxy)butyl 4-t-butylazo-4-cyanovalerate.

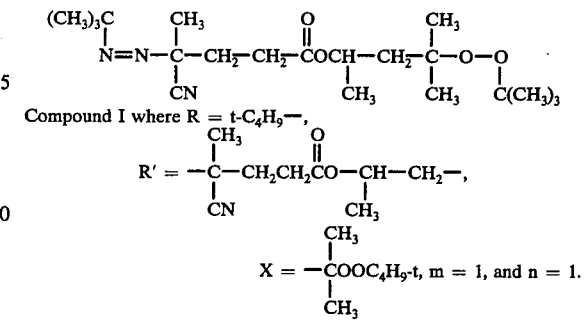

Compound I where R = t-C₄H₉—,
R' = —C(CH₃)(CN)—CH₂CH₂CO—CH(CH₃)—CH₂—,

X = —COOC₄H₉-t, m = 1, and n = 1.

To a solution of 4.15 g. (.0219 m) of 97.5% 2-methyl-2-t-butylperoxy-4-hydroxypentane and 3 ml. of pyridine in 15 ml. either at 5° C was added solution of 5.0g. (0.0219 m) of 4-t-butylazo-4-cyanovaleryl chloride in 10 ml. ether. A white precipitate of pyridine hydrochloride formed immediately. The addition of the acid chloride solution was carried out in 15 minutes at 5° C. The reaction was stirred an additional one hour at room temperature. The reaction mixture was filtered and the ether filtrate washed with 5% HCl, 10% NaHCO₃ solution, water, dried over anhydrous sodium sulfate, filtered and the ether stripped off leaving a light brown liquid weighing 7.4g. (88½% yield).

The product was chromatographed over alumina and eluted with pentane. Upon evaporation of the pentane, 6.3g. of a yellow liquid resulted. The infrared spectrum of the purified product was in agreement with that of the desired product. The product was not shock sensitive.

The azo portion of the molecule has a 10 hour half-life at approximately 76° C while the peroxide portion has a 10 hour half-life at approximately 126° C.

EXAMPLE 11

Preparation of 1,1,4,4-Tetramethyltetramethylene bis(4-t-butylazo-4-cyanoperoxyvalerate)

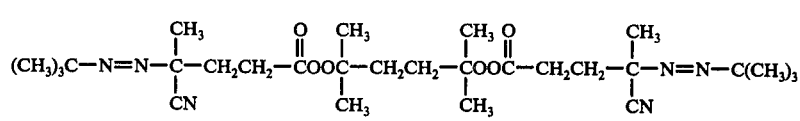

Compound I where R = t-C₄H₉—, R' = 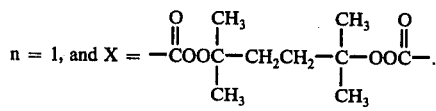, m = 2, n = 1, and X = —COOC(CH₃)₂—CH₂CH₂—C(CH₃)₂—OOC—.

To a solution of 2.72g. (.0152 m) of 2,5-dimethyl-2,5-dihydroperoxyhexane and 5 ml. of pyridine in 30 ml ether at 10° C was added a solution of 7.5g (.0328 m) of 4-t-butylazo-4-cyanovaleryl chloride in 10 mls. ether over 10 minutes. The reaction was stirred an additional hour at room temperature and filtered to remove the precipitated pyridine hydrochloride. The ether filtrate was washed successively with cold 5% KOH, 5% HCl, 10% NaHCO₃ solution, saturated NaCl solution, dried over anhydrous sodium sulfate, filtered and the ether stripped off. A viscous liquid weighing 6.8 g. (79% yield) was obtained. The liquid solidified on standing in the refrigerator. The solid was recrystallized from pentane-benzene to a white crystalline solid with a melting point of 90°-92° C.

The infrared spectrum of the product was in agreement with that of the desired product. An iodometric analysis of the compound indicated there was 5.77% active oxygen present (Theoretical active oxygen = 5.65%). The product was not shock sensitive.

The azo portions of the molecule have a 10 hour half-life at approximately 76° C, while the peroxide portions have a 10 hour half-life at approximately 102° C.

EXAMPLE 12
Preparation of 4,4'-azobis[[1,3-dimethyl-3-(t-butylperoxy)butyl]4-cyanovalerate]

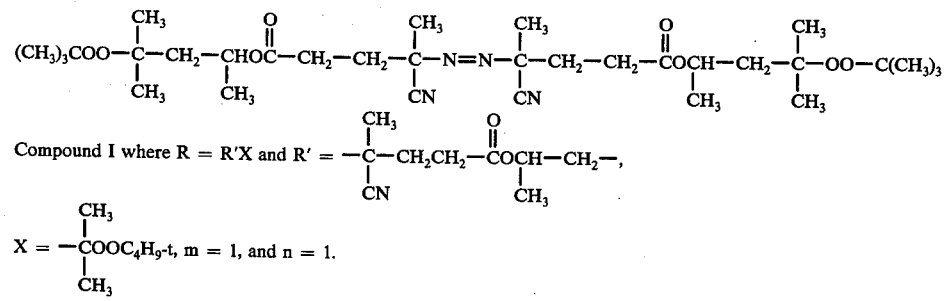

Compound I where R = R'X and R' = —C(CH₃)(CN)—CH₂CH₂—COCH(CH₃)—CH₂—,

X = —COOC₄H₉-t, m = 1, and n = 1.
 (with C(CH₃)₂ group)

To a solution of 4.75g. (.025 m) of 2-methyl-2-t-butylperoxy-4-hydroxypentane and 5 ml. of pyridine in 25 ml. benzene was added a solution of 3.2g. (.01 m) of trans-4,-4'-azobis(4-cyanovaleryl chloride) in 25 ml. benzene at 20° C over 15 minutes holding the temperature at 20° C. The reaction was stirred 1 hour after the acid chloride addition was over. The pyridine hydrochloride was filtered off and the benzene filtrate washed with 5% HCl, 10% NaHCO₃ solution, saturated NaCl solution, dried over anhydrous sodium sulfate, filtered and the benzene stripped off. A viscous liquid weighing 5.2g. (85% yield) was obtained.

The infrared spectrum of the crude material indicated there was some unreacted alcohol present. A sample of 3.4 g of the crude material was dissolved in 5 ml benzene and chromatographed over alumina. The first cut was eluted with 75 ml pentane. Upon evaporation of the pentane 1.9 g of a viscous liquid, which solidified in the refrigerator, was obtained. The infrared spectrum of the product was in agreement with that of the desired product. The second cut contained some of the unreacted alcohol and was discarded.

The azo portion of the molecule has a 10 hour half-life at approximately 65° C while the peroxide portions have a 10 hour half-life at approximately 126° C.

EXAMPLE 13
Preparation of 2,2'-azobis[2-methyl-1-(t-butylperoxycarbonyloxy)propane]

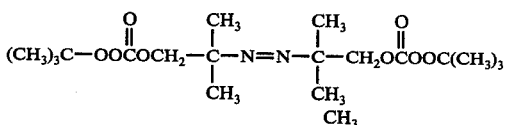

Compound I where R = R'X and R' = —C(CH₃)₂—CH₂—,

X = —O—COOC₄H₉-t, m = 1, and n = 1.

To a solution of 1.8 g (.02 m) of 100% t-butyl hydroperoxide and 1.6 g (.02 m) of pyridine in 25 ml ether at 5° C was added a solution of 3.0 g (.01 m) of 2,2'-azobis(2-methylpropyl chloroformate) in 25 ml ether.

The ether solution of the chloroformate was added dropwise with stirring over 15 minutes, holding the temperature at 5° C. Pyridine hydrochloride began to form immediately. The reaction was stirred an additional ½ hour at 5° C and the pyridine hydrochloride filtered off. The ether solution was washed successively with 2% HCl, 10% NaHCO₃ solution, saturated salt solution, dried over anhydrous sodium sulfate, filtered and the ether stripped off. A liquid weighing 1.8g. (44½% yield) resulted.

The infrared spectrum of the product indicated there was considerable OH present so the product was chromatographed over alumina. The first cut was eluted with 75 ml. pentane. Upon evaporation of the pentane there was 1.25g. of a colorless liquid. An infrared spectrum of this material was in agreement with that of the desired structure, with the exception of a small amount of OH left. The sample was assayed for % t-butylhydroperoxide by a sulfite method and for total active oxygen by a FeCl₃ method. The material assayed 73% as the percarbonate and also contained 1.9% t-butylhydroperoxide.

The azo portion of the molecule has a 10 hour half-life at approximately 162° C while the peroxide portions have a 10 hour half-life at approximately 99° C.

EXAMPLE 14

Preparation of 2,2'-azobis(2-cyano-5-t-butylperoxycarbonyloxypentane)

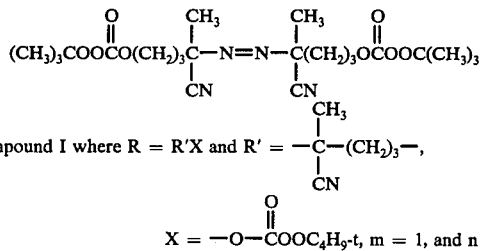

Compound I where R = R'X and R' = —C(CH₃)—(CH₂)₃—,
                                        |
                                        CN X = —O—COOC₄H₉-t, m = 1, and n = 1.

To a solution of 1.9g. (.0212 m) of 100% t-butylhydroperoxide and 1.6g. (.0212 m) of pyridine in 25 ml. ether at 4° C was added a solution of 4g. (.0106 m) of 4,4'-azobis(4-cyanopentyl chloroformate) in 25 ml. ether. The ether solution of the chloroformate was added dropwise with stirring over 15 minutes holding the temperature at 5° C. After the addition was over the reaction was stirred an additional hour at 10° C, the pyridine hydrochloride filtered off, the ether filtrate washed with 5% HCl, 10% NaHCO₃ solution, saturated NaCl solution, dried over anhydrous sodium sulfate, filtered and the ether stripped off. A liquid weighing 3.4g. (67% yield) was obtained.

The infrared spectrum was in agreement with that of the desired product. The product assayed 96½% by an iodometric titration and it was not shock sensitive.

The azo portion of the molecule has a 10 hour half-life at approximately 65° C while the peroxide portions have a 10 hour half-life at approximately 99° C.

EXAMPLE 15

Preparation of Di(4-t-butylazo-4-cyanopentyl) peroxydicarbonate

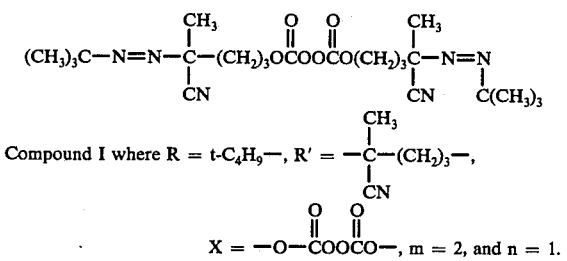

Compound I where R = t-C₄H₉—, R' = —C(CH₃)—(CH₂)₃—,
                                      |
                                      CN X = —O—COOCO—, m = 2, and n = 1.

To a solution of 10.2g. (.0395 m) of 4-t-butylazo-4-cyanopentyl chloroformate in 30 ml. ether at 5° C was added dropwise with stirring a solution of 1.97g. (.022m) of 38% hydrogen peroxide, and 3.3g. (.042 m) of pyridine in 10 ml. ether. The temperature was held below 10° C during the addition period. The reaction was stirred an additional ½ hour at 10° C, the pyridine hydrochloride filtered off and the ether filtrate washed with 2% HCl, 10% NaHCO₃ solution, saturated NaCl solution, dried over anhydrous sodium sulfate, filtered and the ether stripped off. A liquid weighing 7.55g. (80% yield) was obtained.

The infrared spectrum of the product was in agreement with that of the desired product except for some OH present. The sample assayed 60% by iodometric titration and was not shock sensitive.

The azo portions of the molecule have a 10 hour half-life at approximately 78° C while the peroxide portion has a 10 hour half-life at approximately 45° C.

EXAMPLE 16

Preparation of 0-4-t-Butylazo-4-cyanopentyl 0,0-t-butylmonoperoxycarbonate

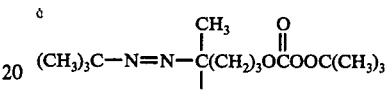

Compound I where R = t-C₄H₉—, R' = —C(CH₃)—(CH₂)₃—,
                                      |
                                      CN X = OCOOC₄H₉-t, m = 1, and n = 1.

To a solution of 1.8 g. (.02 m) of 100% t-butyl hydroperoxide and 1.6 g. (.02 m) of pyridine in 25 ml. ether at 5° C was added dropwise with stirring a solution of 5.2 g. (.02 m) of 4-t-butylazo-4-cyanopentyl chloroformate in 25 ml. ether. After the addition was complete, the reaction was stirred an additional hour at 10° C, the pyridine hydrochloride was filtered off and the ether layer was successively washed with 5% HCl, 10% NaHCO₃ solution and saturated NaCl solution, dried over anhydrous sodium sulfate, filtered and the ether stripped off. A liquid weighing 5.8 g. (92% yield) was obtained.

The infrared spectrum of the product was in agreement with that of the desired product and the material was not shock sensitive. It assayed 80.0% by iodometric titration.

The azo portion of the molecule has a 10 hour half-life at approximately 78° C while the peroxide portion has a 10 hour half-life at approximately 99° C.

EXAMPLE 17

A. Preparation of a Peroxide-Containing polystyrene from 1,3-Dimethyl-3-(t-butylperoxy)butyl 4-t-Butylazo-4-cyanovalerate.

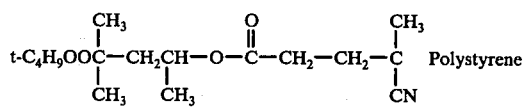

A mixture of 15 g. of styrene and 3 g. of 1,3-dimethyl-3-(t-butylperoxy)butyl 4-t-butylazo-4-cyanovalerate, from Example 10, in 36 g. of xylene was heated at 90° C under nitrogen for 6 hours. The cooled reaction mixture was precipitated in odorless mineral spirits. The resultant polymer was dissolved in benzene and reprecipitated from mineral spirits three times. The purified peroxide-containing-polymer weighed 13.1 g.

B. Preparation of a Polystyrene-Poly(methyl methacrylate) Block Copolymer from the Peroxide Containing Polystyrene of A.

A mixture of 15 g. of methyl methacrylate and 3 g. of the above peroxide containing polystyrene in 36 g. xylene was heated for 1 hour at 120° C and 7 hours at 129° C under nitrogen in a sealed tube. The cooled reaction mixture was precipitated in odorless mineral spirits. The resultant polymer was dissolved in benzene and reprecipitated from mineral spirits twice. The dried product weighed 12 g.

A 14% solution of the final product in chloroform did not demix in thirteen days. A 1:1 mixture of 14% polystyrene in chloroform and 14% poly(methyl methacrylate) in chloroform demixed in 15 minutes. These tests indicate that the block copolymer was formed.

Additional species, coming within the scope of this invention, were also prepared, and are listed in Table III below. As with the previous examples, proof of structure was accomplished by means of Infrared spectroscopy and active oxygen analysis where applicable methods were available. The methods of preparation of some of these compounds follow the table.

Table III

| Example | Structure and Name | Form | Shock Sensitivity | Gas Evolution Temperature | Ten Hour Half-Life Temperature Azo | Ten Hour Half-Life Temperature Peroxide |
|---|---|---|---|---|---|---|
| 18 | 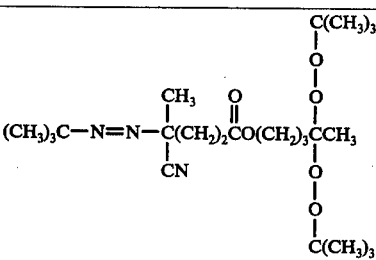 4,4-bis(t-butylperoxy)pentyl 4-(t-butylazo)-4-cyanovalerate | liquid | negative | 90–100° C | ≈76° C | ≈101–110° C |
| 19 | 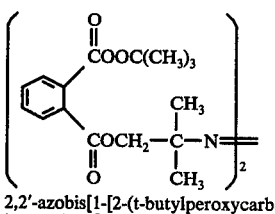 2,2'-azobis[1-[2-(t-butylperoxycarbonyl)-benzoyloxy]-2-methylpropane] | liquid | negative | 140° C | ≈162° C | ≈105° C |
| 20 | 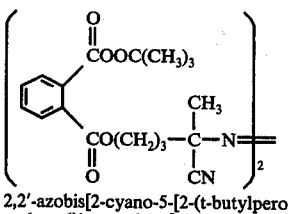 2,2'-azobis[2-cyano-5-[2-(t-butylperoxy-carbonyl)benzoyloxy]pentane] | liquid | negative | 70° C | ≈65° C | ≈105° C |
| 21 | 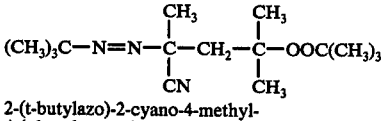 2-(t-butylazo)-2-cyano-4-methyl-4-(t-butylperoxy)pentane | liquid | negative | 70° C | ≈55–60° C | ≈126° C |
| 22 | 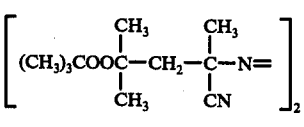 2,2'-azobis[2-cyano-4-methyl-4-(t-butylperoxy)-pentane] | Two solid isomers I-m.p. 51–53° C DEC. II-m.p. 87–88° C DEC. | negative negative | 55° C 90° C | ≈40° C ≈40° C | ≈126° C ≈126° C |
| 23 | 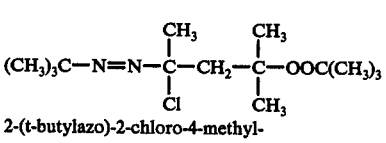 2-(t-butylazo)-2-chloro-4-methyl- | liquid | negative | 35° C | ≈60° C | ≈126° C |

Table III-continued

Azo-Peroxides

| Example | Structure and Name | Form | Shock Sensitivity | Gas Evolution Temperature | Ten Hour Half-Life Temperature | |
|---|---|---|---|---|---|---|
| | | | | | Azo | Peroxide |
| | 4-(t-butylperoxy)-pentane | | | | | |
| 24 | $(CH_3)_3C-N=N-\underset{\underset{CH_3}{O}}{\overset{CH_3}{C}}-CH_2-\underset{CH_3}{\overset{CH_3}{C}}-OOC(CH_3)_3$<br>2-(t-butylazo)-2-methoxy-4-methyl-4-(t-butylperoxy)-pentane | liquid | negative | 70° C | ≈75° C | ≈126° C |
| 25 | $(CH_3)_3C-N=N-\underset{N_3}{\overset{CH_3}{C}}-CH_2-\underset{CH_3}{\overset{CH_3}{C}}-OOC(CH_3)_3$<br>2-(t-butylazo)-2-azido-4-methyl-4-(t-butylperoxy)pentane | liquid | negative | 45° C | ≈60° C | ≈126° C |
| 26 | $(CH_3)_3C-N=N-\underset{\underset{\underset{CH_3}{C=O}}{O}}{\overset{CH_3}{C}}-CH_2-\underset{CH_3}{\overset{CH_3}{C}}-OOC(CH_3)_3$<br>2-(t-butylazo)-2-acetoxy-4-methyl-4-(t-butylperoxy)-pentane | liquid | negative | 90° C | ≈100° C | ≈126° C |
| 27 | $(CH_3)_3C-N=N-\underset{Br}{\overset{CH_3}{C}}-CH_2-\underset{CH_3}{\overset{CH_3}{C}}-OOC(CH_3)_3$<br>2-(t-butylazo)-2-bromo-4-methyl-4-(t-butylperoxy)-pentane | liquid | negative | <10° C | <10° C | ≈126° C |
| 28 | $HOO-\underset{CH_3}{\overset{CH_3}{C}}-\underset{CN}{\overset{CH_3}{C}}-N=N-\underset{CN}{\overset{CH_3}{C}}-\underset{CH_3}{\overset{CH_3}{C}}-OOH$<br>2,2'-azobis(2-cyano-3-methyl-3-hydroperoxybutane) | liquid | negative | 70° C | ≈65° C | ≈160-170° C |
| 29 | $(CH_3)_3C-N=N-\underset{\underset{C_6H_5}{O}}{\overset{CH_3}{C}}-CH_2-\underset{CH_3}{\overset{CH_3}{C}}-OO-C(CH_3)_3$<br>2-(t-Butylazo)-2-phenoxy-4-methyl-4-(t-butylperoxy)-pentane | liquid | negative | ~105° | ~110° C | ~126° C |
| 30 | $(CH_3)_3C-N=N-\underset{S}{\overset{CH_3}{C}}-CH_2-\underset{CH_3}{\overset{CH_3}{C}}-OO-C(CH_3)_3$<br>with S attached to p-(C(CH₃)₃)-phenyl<br>2-(t-Butylazo)-2(p-t-butylthio-phenoxy)-4-methyl-4-(t-butylperoxy)-pentane | liquid | negative | ~90° | ~95° C | ~126° C |
| 31 | $(CH_3)_3C-N=N-\underset{\underset{\underset{N}{\overset{\|\|\|}{C}}}{S}}{\overset{CH_3}{C}}-CH_2-\underset{CH_3}{\overset{CH_3}{C}}-OO-\underset{CH_3}{\overset{CH_3}{C}}-CH_3$<br>2-(t-Butylazo)-2-thiocyanato-4-methyl-4-(t-butylperoxy)pentane | liquid | negative | ~70 | ~75° C | ~126° C |

Table III-continued
Azo-Peroxides

| Example | Structure and Name | Form | Shock Sensitivity | Gas Evolution Temperature | Ten Hour Half-Life Temperature | |
|---|---|---|---|---|---|---|
| | | | | | Azo | Peroxide |
| 32 | $(CH_3)_3C-N=N-\underset{\underset{\underset{CH_3}{\mid}}{\underset{(CH_2)_{11}}{\mid}}{\overset{CH_3}{\mid}}}{C}-CH_2-\underset{\overset{CH_3}{\mid}}{\overset{CH_3}{\mid}}{C}-OO-C(CH_3)_3$ <br> 2-(t-Butylazo)-2-dodecanethiol-4-methyl-4-(t-butylperoxy)pentane | liquid | negative | ~85° | ~90° C | ~126° C |
| 33 | $(CH_3)_3C-N=N-\underset{\underset{\underset{CH_3}{\mid}}{\underset{C=O}{\mid}}{\overset{CH_3}{\mid}}}{C}-CH_2-\underset{\overset{CH_3}{\mid}}{\overset{CH_3}{\mid}}{C}-OO-C(CH_3)_3$ <br> 2-(t-Butylazo)-2-thioacetoxy-4-methyl-4-(t-butylperoxy)pentane | liquid | negative | ~115° | ~120° C | ~126° C |
| 34 | $(CH_3)_3C-N=N-\underset{\overset{C_6H_5}{\mid}}{\overset{CH_3}{\mid}}{C}-CH_2-\underset{\overset{CH_3}{\mid}}{\overset{CH_3}{\mid}}{C}-OO-C(CH_3)_3$ <br> 2-(t-Butylazo)-2-phenyl-4-methyl-4-(t-butylperoxy)pentane | liquid | negative | ~55° | ~57° C | ~126° C |
| 35 | $(CH_3)_3C-N=N-\underset{\underset{\underset{C(CH_3)_3}{\mid}}{\underset{O}{\mid}}{\overset{O}{\mid}}}{\overset{CH_3}{C}}-CH_2-\underset{\overset{CH_3}{\mid}}{\overset{CH_3}{\mid}}{C}-OO-C(CH_3)_3$ <br> 2-(t-Butylazo)-2,4-di-(t-butylperoxy)-4-methylpentane | liquid | negative | ~30° | ~25° C | ~126° C |
| 36 | $(CH_3)_3C-N=N-\underset{\overset{S}{\underset{C_6H_5}{\mid}}}{\overset{CH_3}{\mid}}{C}-CH_2-CH_2-\overset{O}{\overset{\|}{C}}OOC(CH_3)_3$ <br> t-Butyl 4-(t-butylazo)-4-(thiophenoxy)peroxyvalerate | liquid | negative | ~100° | ~130° C | ~105° C |
| 37 | $\left[(CH_3)_3C-N=N-\underset{\overset{S}{\underset{C_6H_5}{\mid}}}{\overset{CH_3}{\mid}}{C}-CH_2-CH_2-\overset{O}{\overset{\|}{C}}O-\right]_2$ <br> Di [4-t-(butylazo)-4-(thiophenoxy)valeryl]peroxide | liquid | negative | ~40° | ~130° C | ~45° C |
| 38 | $(CH_3)_3C-N=N-\underset{\overset{S}{\underset{\text{—C}_6H_4\text{—}C(CH_3)_3}{\mid}}}{\overset{CH_3}{\mid}}{C}-CH_2-CH_2-\overset{O}{\overset{\|}{C}}OOC(CH_3)_3$ <br> t-Butyl 4-(t-butylazo)-4-(p-t-butylthiophenoxy)peroxyvalerate | liquid | negative | ~100° | ~130° C | ~105° C |

Table III-continued
Azo-Peroxides

| Example | Structure and Name | Form | Shock Sensitivity | Gas Evolution Temperature | Ten Hour Half-Life Temperature Azo | Ten Hour Half-Life Temperature Peroxide |
|---|---|---|---|---|---|---|
| 39 | [(CH$_3$)$_3$C—N≡N—C(CH$_3$)(S-C$_6$H$_4$-C(CH$_3$)$_3$)—CH$_2$—CH$_2$—C(O)—O]$_2$<br>Di[4-t-(butylazo)-4-(p-t-butylthiophenoxy)valeryl)]peroxide | solid | negative | ~40° | ~130° C | ~45° C |
| 40 | [(CH$_3$)$_3$C—N≡N—C(CH$_3$)(N$_3$)—CH$_2$—CH$_2$—C(O)—O]$_2$<br>Di[4-(t-butylazo)-4-azidovaleryl] peroxide | liquid | negative | ~45° | ~100° C | ~50° C |
| 41 | (CH$_3$)$_3$C—N=N—C(CH$_3$)(N$_3$)—CH$_2$—CH$_2$—COOC(CH$_3$)$_3$<br>t-Butyl 4-(t-butylazo)-4-azido-peroxyvalerate | liquid | negative | ~100° | ~110° C | ~106° C |
| 42 | (CH$_3$)$_3$C—N=N—C((CH$_2$)$_5$)((CH$_2$)$_{10}$)(CN)—COOC(CH$_3$)$_3$<br>t-Butyl 12-(t-butylazo)-12-cyano-peroxystearate | liquid | negative | ~80° | ~76° C | ~106° C |
| 43 | (CH$_3$)$_3$C—N=N—C(CH$_3$)(N$_3$)—CH$_2$—CH$_2$—COOC(CH$_3$)$_2$—CH$_2$—C(CH$_3$)$_3$<br>1,1,3,3-Tetramethylbutyl 4-(t-butylazo)-4-azidoperoxyvalerate | liquid | negative | ~100° C | ~110° C | ~100° C |
| 44 | (CH$_3$)$_3$C—N=N—C(CH$_3$)(S-C$_6$H$_4$-C(CH$_3$)$_3$)—CH$_2$—CH$_2$—COOC(CH$_3$)$_2$—CH$_2$—C(CH$_3$)$_3$<br>1,1,3,3-Tetramethylbutyl 4-(t-butylazo)-4-(p-t-butylthiophenoxy)peroxyvalerate | liquid | negative | ~120° C | ~130° C | ~100° C |
| 45 | (CH$_3$)$_3$C—N≡N—C(CH$_3$)(CN)—CH$_2$—CH$_2$—COOC(CH$_3$)$_2$—CH$_2$—C(CH$_3$)$_3$<br>1,1,3,3,-Tetramethylbutyl 4-(t-butylazo)-4-cyanoperoxyvalerate | liquid | negative | 85° C | ~76° C | ~100° C |

The following are descriptions of the procedures used to prepare many of the compounds in Table III.

EXAMPLE 21

Preparation of 2-(t-Butylazo)-2-cyano-4-methyl-4-(t-butylperoxy)pentane

The t-butylhydrazone of 4-methyl-4-(t-butylperoxy)-3-pentanone was prepared by the method described in Example 23 (below). To 21 g. of the above butylhydrazone in a 60 ml. pressure bottle was added 10 ml. liquid HCN and the bottle stoppered and allowed to stand overnight. The next morening the solution was poured into 200 ml. water and extracted with pentane. The pentane layer was washed twice with 50 ml. of saturated NaHCO$_3$ solution and placed in a 500 ml. 4-neck round bottom flask with 50 ml. of water. The temperature was lowered to 5° C. with an ice bath and then chlorine passed into the system holding the temperature below 10° C. After 5.5 grams of chlorine had been added, the exotherm ceased. The chlorine addition was stopped and the reaction allowed to stir an additional ½ hour, the pentane layer separated, washed successively with water, saturated NaHCO$_3$ solution, water, dried over anhydrous sodium sulfate, filtered and the pentane evaporated on a flash evaporator. The residue weighed 14.1 g and was a mixture of the desired product, 4-methyl-4-(t-butylperoxy)-2-pentanone and some tarry materials. The desired product was isolated by column chromatography over alumina with pentane as the eluent.

EXAMPLE 22

The compound of Example 22 was prepared in a similar manner from the ketazine of 4-methyl-4-(t-butylperoxy)-2-pentanone and liquid HCN followed by oxidation with aqueous chlorine.

EXAMPLE 23

Preparation of
2-(t-butylazo)-2-chloro-4-methyl-4-(t-butylperoxy)pentane

4-Methyl-4-(t-butylperoxy)-2-pentanone was prepared by the addition of t-butylhydroperoxide to mesityl oxide. The t-butylhydrazone of 4-methyl-4-(t-butylperoxy)-2-pentanone was prepared by refluxing a solution of equimolar amounts of t-butylhydrazine and 4-methyl-4-(t-butylperoxy)-2-pentanone for 2 hours.

To a solution of 5.16 g. (0.02 moles) of the t-butylhydrazone of 4-methyl-4-(t-butylperoxy)-2-pentanone in 25 ml. of pentane in a 100 ml. 4-neck flask, precooled to 0° C, was added 1.42 g. (0.02 moles) of chlorine over a 15 minute period. The reaction was stirred for an additional ½ hour at 0° C and then filtered to remove the white solid which formed during the chlorination. The pentane filtrate was evaporated on a flash evaporator to give 3.8 grams (65% yield) of the desired product.

EXAMPLE 27

The 2-bromo derivative of Example 27 was prepared in a similar manner to the 2-chloro derivative of Example 23 by the addition of bromine instead of chlorine.

EXAMPLE 28

Preparation of
2,2'-Azobis(2,3-dimethyl-3-hydroperoxybutyronitrile)

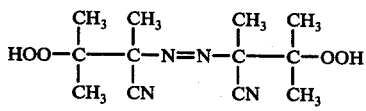

(A) Preparation of 2,2'-Azobis(2,3-dimethyl-3-hydroxybutyronitrile)

The ketazine of methyl hydroxy butanone was prepared in 98% yield by refluxing 0.1 moles of 85% hydrazine hydrate and 0.2 moles of methyl hydroxy butanone with 25 ml. of benzene and removing the water formed by means of a Dean Stark trap.

To a pressure bottle containing 18.7 g of the above ketazine, was added 25 ml. of liquid HCN, the bottle stoppered and allowed to stand overnight at room temperature. Upon standing overnight a solid crystallized out. The liquid portion was decanted into a stirred solution of NaOH to convert the HCN to NaCN. The solid was broken up, slurried in 50 ml. water, filtered and dried. It weighed 14.8 g. and had a melting point of 145°-147° C.

The hydrazo was oxidized with chlorine in a methylene chloride-water system, washed with saturated NaHCO$_3$ solution, and the methylene chloride solution of the azo dried, filtered and the methylene chloride evaporated on a rotating evaporator. The product weighed 14.4 g and had a melting point of 123°-125° C.

(B) Preparation of 2,2'-Azobis(2,3-dimethyl-3-hydroperoxybutyronitrile)

To 14.0 g of 70% H$_2$SO$_4$ which was stirred and cooled to 0° C was added dropwise 15.8 grams of 50% H$_2$O$_2$ followed by 40 ml. CH$_2$Cl$_2$. To the stirred reaction mixture was added portionwise 15.1 grams (0.06 moles) of 2,2'-azobis (2,3-dimethyl-3-hydroxybutyronitrile) over ½ hour at 1° C. The temperature was allowed to rise from 1° to 25° over a 2 hour period and then stirred at 25° for 3 hours longer. The methylene chloride layer was separated, washed with 40% (NH$_4$)$_2$SO$_4$ solution, water, dried over anhydrous magnesium sulfate filtered and the methylene chloride evaporated on a rotating evaporator to leave 13.0 grams of a mushy solid. The solids were slurried up in pentane and refiltered to give 10 grams of a white solid melting at 83°-85° C. The solid assayed 74% as the desired product by iodometric titration. The pentane filtrate was evaporated to dryness to give 2.5 grams of a liquid which assayed 70.7% as the desired product. Infrared analysis indicated that the two materials were most likely isomers.

EXAMPLE 30

Preparation of
2-(t-butylazo)-2-(p-t-butylthiophenoxy)-4-methyl-4-(t-butylperoxy)pentane

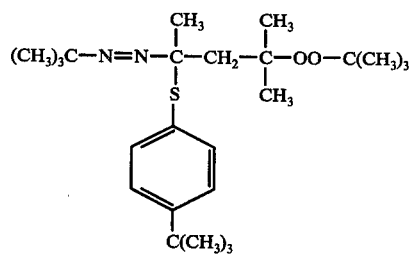

To a stirred solution of 1.38 g (0.021 moles) of 85% potassium hydroxide in 25 ml. of methanol in a 125 ml. erlenmeyer flask was added dropwise 3.66 grams (0.022 moles) of p-t-butylthiophenol. The reaction was stirred an additional 30 minutes and then 6.0 grams (0.0205 moles) of 2-(t-butylazo)-2-chloro-4-methyl-4-(t-butylperoxy)pentane from Example 23 was added dropwise over 30 minutes, holding the reaction temperature at 15° C with a cold water bath. The reaction was stirred an additional hour at room temperature and poured into 100 ml. of water. The product was extracted with 50 ml. of pentane, the pentane solution washed with water, dried over anhydrous sodium sulfate, filtered and the pentane evaporated on a flash evaporator. The residue weighed 8.65 g (72% yield) and its infrared spectrum was in agreement with that of the desired product.

EXAMPLES 24, 25, 26, 29, 31, 32, 33 and 35

The 2-methyl, 2-azido, 2-acetoxy, 2-phenoxy, 2-thiocyanato, 2-dodecanethiol, 2-thioacetoxy and 2-t-butylperoxy derivatives of Examples 24, 25, 26, 29, 31, 32, 33 and 35 were prepared by similar reactions, i.e. reacting the 2-(t-butylazo)-2-chloro-4-methyl-4-(t-butylperoxy)-pentane (from Example 23) with approximately equivalent amounts of the corresponding sodium or potassium salt in alcohol i.e. either sodium or potassium methoxide, azide, acetate, phenate, thiocyanate, thiododecanoxide, thioacetate, and t-butyl hydroperoxide.

EXAMPLE 34

Preparation of 2-(t-butylazo)-2-phenyl-4-methyl-4-(t-butylperoxy)pentane

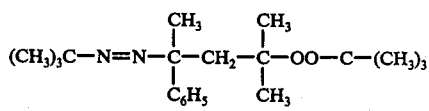

To a solution of 8.0 grams (0.0274 moles) of 2-(t-butylazo)-2-chloro-4-methyl-4-(t-butylperoxy)pentane (from Example 23) in 150 ml. of pentane in a clean, dry, nitrogen purged 500 ml. reaction flask equipped with a mechanical stirrer, thermometer, and condenser with drying tube, was slowly added 9.3 ml. (0.028 moles) of a 3 molar ether solution of phenyl magnesium bromide. The reaction temperature was kept at 20° to 25° C, with a cold water bath. After the addition was complete, the reaction mixture was stirred an additional 30 minutes at 15° C. Ice chips were then added to the reaction to slowly destroy the excess phenyl magnesium bromide. The reaction mixture was poured into 200 ml. of water, the pentane layer separated and washed successively with 10% HCl, water, saturated NaHCO$_3$ solution and water. The pentane solution was dried over anhydrous sodium sulfate, filtered and the pentane evaporated on a flash evaporator. The residue weighed 5.7 grams (62% yield) and the infrared spectrum was in agreement with the structure of the desired compound.

EXAMPLES 36 to 45

The compounds of examples 36 to 45 were prepared from the corresponding azo acid chlorides using the procedure described in Example 8 for the azo-diacyl peroxides and the procedure described in Example 9 for the azo-peroxyesters.

Many compounds of the present invention are taught in the above examples. Some additional compounds of the subject invention which may likewise be prepared are illustrated below and many more will be obvious to those skilled in the art:

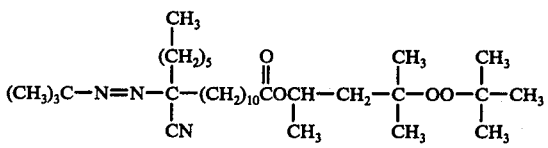

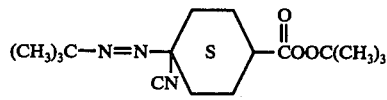

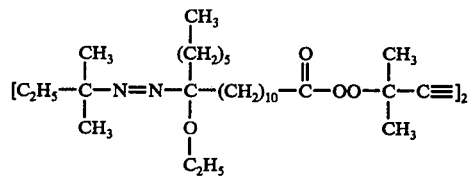

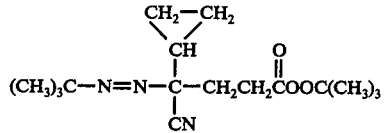

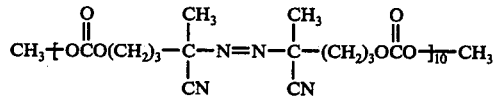

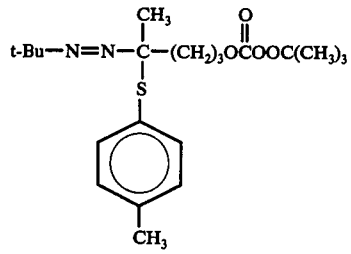

-continued
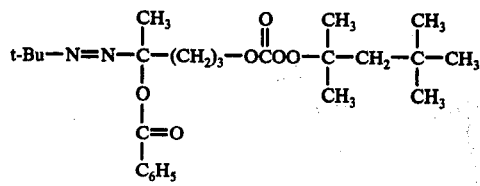
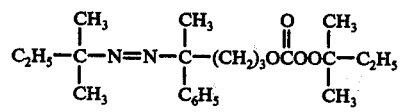
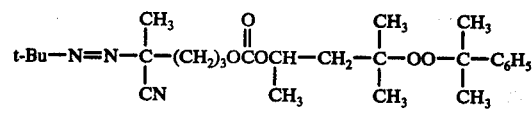
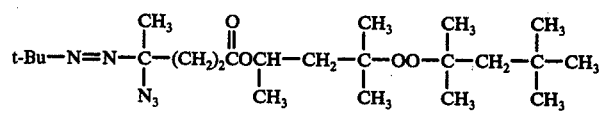
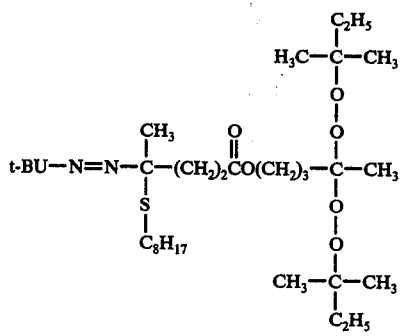
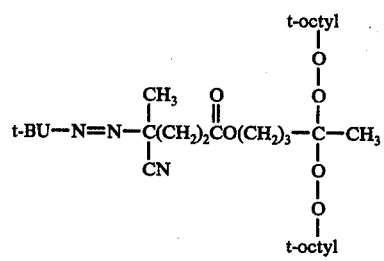
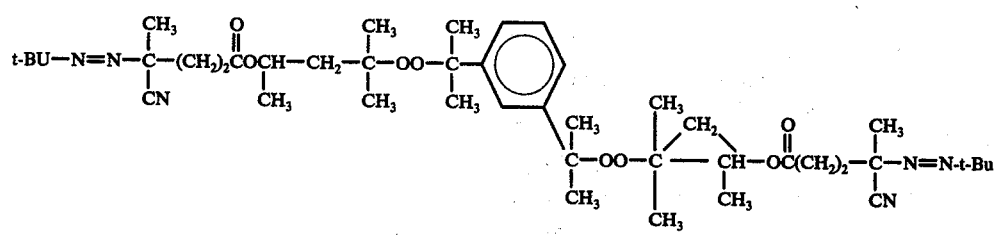
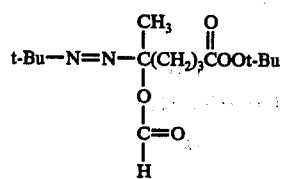

-continued
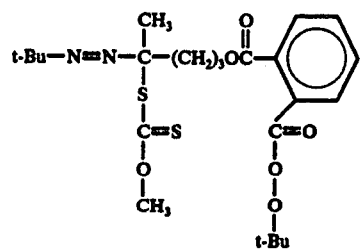
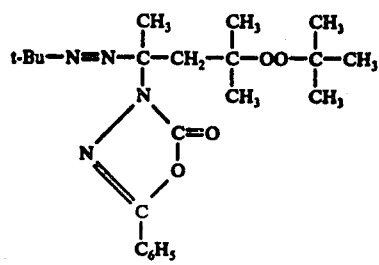
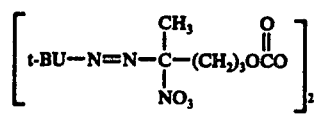
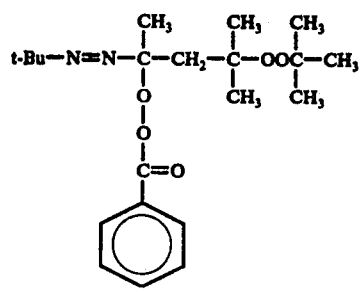
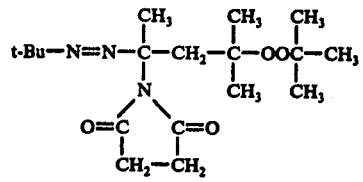
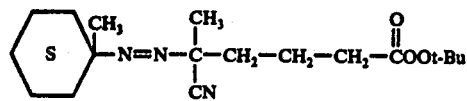
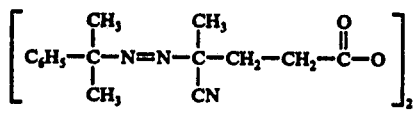
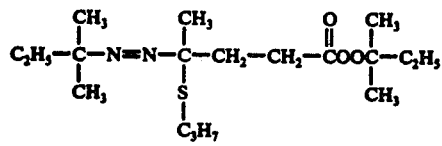
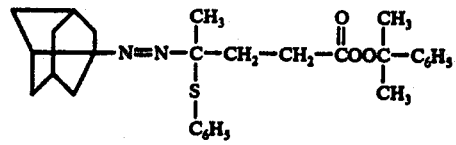

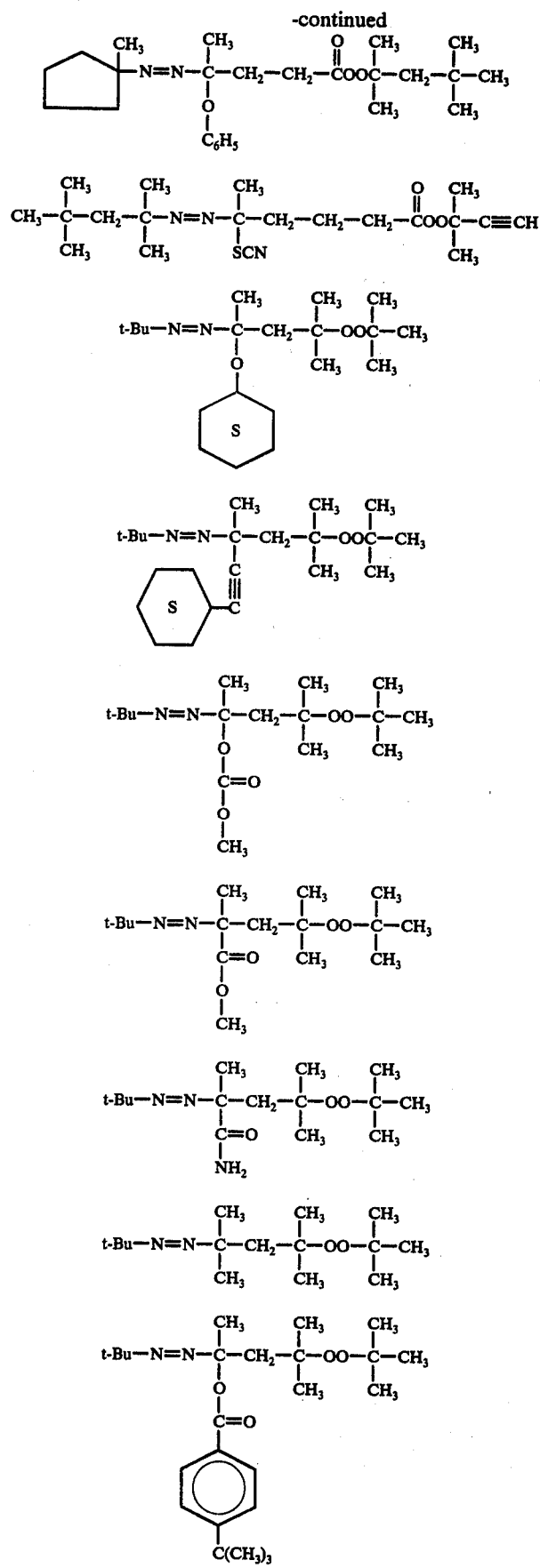

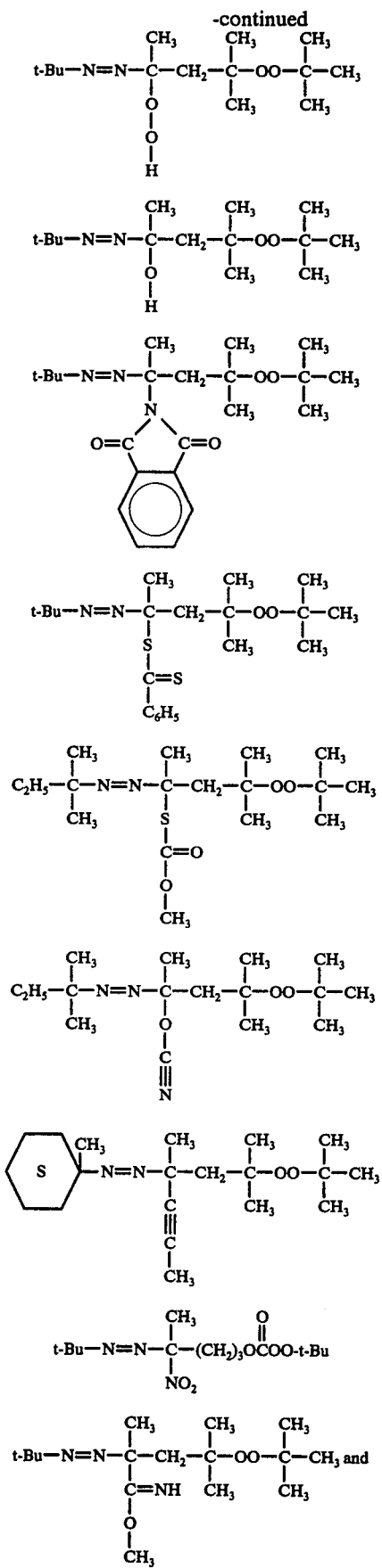

-continued

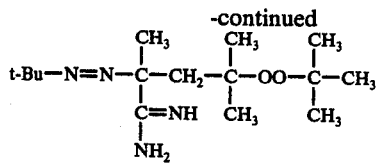

In addition to the $R_5$ diradicals contained in the compounds specifically exemplified hereinabove, some other $R_5$ diradicals falling within the scope of this invention are illustrated below:

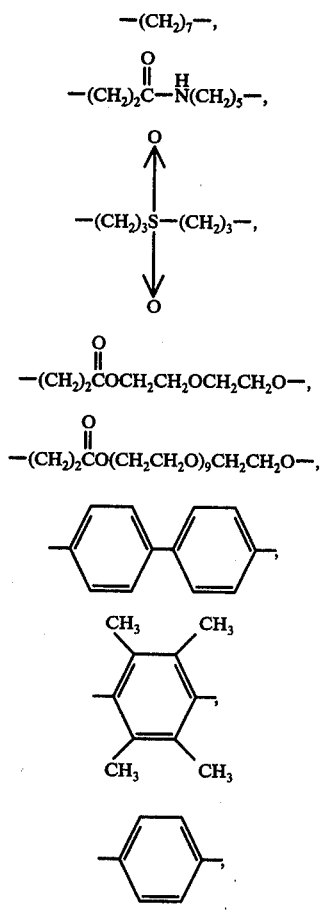

We claim:
1. A compound, having idependent peroxidic and aliphatic azo groups, of the formula $(R-N=N-R'-)_2 X$ where:
(1) R' is

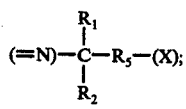

(2) X is a peroxy containing diradical selected from $-C(=O)OOC(=O)-$, $-OC(=O)OOC(=O)O-$ and

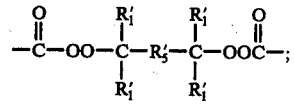

(3) $R_1$ and $R_1'$ can be the same or different and are alkyl or cycloalkyl radicals having 1-10 carbon atoms;
(4) $R_2$ is selected from

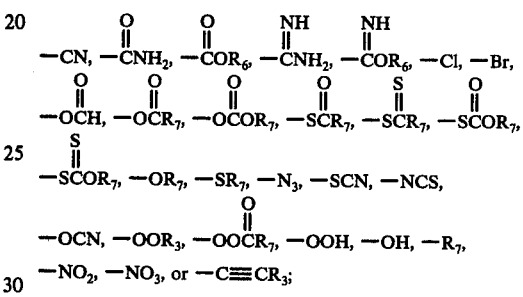

(5) $R_3$ is a tertiary aliphatic radical having 4-10 carbon atoms;
(6) $R_5$ and $R_5'$ may be the same or different and are aliphatic diradicals having 1-20 carbons optionally containing in the backbone structure one or more non-adjacent oxygen, sulfur or nitrogen atoms; aromatic diradicals having 6-12 carbons; or aromatic-aliphatic diradicals having 7-20 carbons optionally containing in the backbone structure one or more non-adjacent oxygen, sulfur or nitrogen atoms;
(7) $R_6$ is a lower alkyl radical;
(8) $R_7$ is an alkyl or cycloalkyl radical of 1-10 carbons or an aromatic radical of 6-12 carbons;
(9) $R_1$ and $R_5$ together with the tertiary carbon atoms in R' can form a cycloalkyl triradical of 3-10 carbons; and
(10) R is a tertiary aliphatic radical of 4-10 carbons.

2.

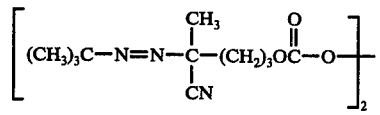

3.

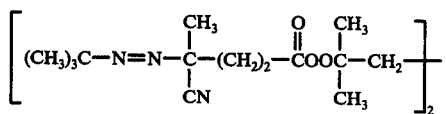

4.

5.
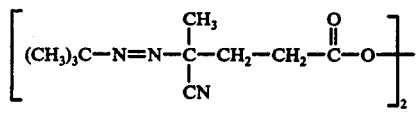
6.
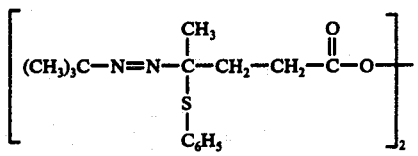
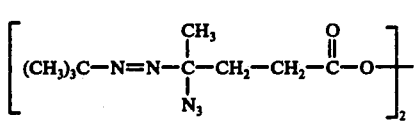
* * * * *